US012768766B2

(12) United States Patent
Chang et al.

(10) Patent No.: US 12,768,766 B2
(45) Date of Patent: Oct. 20, 2026

(54) MECHANISM TO ALLOW LOW DIFFERENTIAL PRESSURE MEASUREMENT DURING FLUID FLOW

(71) Applicant: ARAMCO SERVICES COMPANY, Houston, TX (US)

(72) Inventors: Fakuen Frank Chang, Houston, TX (US); Chao Liu, Brookshire, TX (US); Tim Luce, Houston, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 336 days.

(21) Appl. No.: 18/660,734

(22) Filed: May 10, 2024

(65) Prior Publication Data

US 2025/0347606 A1 Nov. 13, 2025

(51) Int. Cl.
*G01N 15/08* (2006.01)
*G01N 33/24* (2006.01)

(52) U.S. Cl.
CPC ..... *G01N 15/0826* (2013.01); *G01N 15/0806* (2013.01); *G01N 33/24* (2013.01)

(58) Field of Classification Search
CPC . G01N 15/0826; G01N 15/0806; G01N 33/24
See application file for complete search history.

(56) References Cited

U.S. PATENT DOCUMENTS 10,168,265 B2 1/2019 Dwarakanath et al.
10,502,673 B2 * 12/2019 Chertov ............... G01N 15/088
11,585,741 B2 2/2023 Linnemeyer et al.
2019/0353575 A1 * 11/2019 Clarkson ............ G01N 15/0826
2020/0370989 A1 * 11/2020 Zhang .................. G01N 15/082

FOREIGN PATENT DOCUMENTS

CN 105758582 B 2/2019
WO WO-2020154197 A1 * 7/2020 ............... G01F 1/42

OTHER PUBLICATIONS

Zhu, et al., A Semi-analytical Model for Pressure-Dependent Permeability of Tight Sandstone Reservoirs, Springer Sciencet + Business Media B.V., 2018 (18 pages).
An, et al., "Non-Klinkenberg slippage phenomenon at high pressure for tight core floods using a novel high pressure gas permeability measurement system," Journe of Petroleum Science and Engineering, 2017 (5 pages).

* cited by examiner

*Primary Examiner* — Francis C Gray
(74) *Attorney, Agent, or Firm* — Osha Bergman Watanabe & Burton LLP

(57) ABSTRACT

Systems and methods for measuring permeability of a porous medium including injecting a fluid into a flow manifold via an inlet line and subsequently into a first branch and second branch of the flow manifold and measuring a first flow rate of the fluid in the first branch. The fluid is fed through a first coil and a second coil disposed in the second branch and through a control coil and a porous medium in the first branch. The method also includes measuring a second flow rate of fluid flowing through a cross flow line, adjusting the first flow rate until the second flow rate is equal to zero, calculating a transmissibility of the first coil, the second coil, and the control coil, and calculating a permeability of the porous medium.

15 Claims, 2 Drawing Sheets

MECHANISM TO ALLOW LOW DIFFERENTIAL PRESSURE MEASUREMENT DURING FLUID FLOW

BACKGROUND

Permeability of a geological formation refers to the capacity of a porous material to allow fluids to pass through the formation. Permeability is an intrinsic property of porous materials and depends on the number, geometry, and size of interconnected pores, as well as capillaries and fractures within the formation. Determining permeability of geological formations is important because permeability determines the case at which fluids, such as oil and gas, flow through the geological formation.

Permeability may be measured in a laboratory by flowing a single-phase fluid with a known viscosity at a set flow rate through a rock core of known length and diameter. Corrections are then applied to the laboratory measured permeability value to account for differences in laboratory versus downhole conditions. In the field, permeability may be estimated using well logging data. In this case, permeability is typically estimated from nuclear magnetic resonance tools and requires knowledge of the empirical relationship between computed permeability, porosity, and pore-size distribution. Often, permeability estimations in the field are calibrated to direct core sample measurements from nearby wells. On the reservoir scale, permeability is typically determined with drillstem tests (DSTs). DSTs provide a pressure transient analysis of reservoir formations which may be used to assess the average in-situ permeability of the reservoir. Transient behavior may then be estimated by flow rate and pressure during steady-state production.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a system for measuring permeability of a porous medium, including an inlet line having an inlet pressure gauge, where a fluid is injected into the inlet line and a flow manifold. The flow manifold includes a first branch having a first inlet line having a first flow meter, a pressure control system, located downstream of the first flow meter, where the pressure control system includes a control coil and a flow control device located immediately downstream of the control coil, a first flow line, exiting the pressure control system, and a first junction point, fluidly connected to the first flow line and a cross flow line, where the cross flow line comprises a second flow meter, a porous medium, located downstream of the first junction point, and a first outlet line. The first flow line enters the porous medium and the first outlet line exits the porous medium. The flow manifold also includes a second branch, including a second inlet line, a first coil, where the second inlet line is fluidly connected to an upstream side of the first coil, a second flow line, exiting the first coil, a second junction point, fluidly connected to the first flow line through the cross flow line, a second coil, where the second flow line enters the second coil, and a second outlet line exiting the second coil, where the cross flow line connects the first branch to the second branch, and an effluent line, where the first outlet line and the second outlet line combine to produce the effluent line.

In another aspect, embodiments disclosed herein relate to a method for measuring permeability of a porous medium, including injecting a fluid into a flow manifold via an inlet line fluidly connected to the flow manifold, feeding a first portion of the fluid into a first inlet line in a first branch of the flow manifold, feeding a second portion of the fluid into a second inlet line in a second branch of the flow manifold, and measuring a first flow rate of the first portion of the fluid using a first flowmeter disposed on the first inlet line. The method also includes feeding the second portion of the fluid through a first coil and a second coil, successively, disposed in the second branch of the flow manifold, feeding the first portion of the fluid through a control coil and a porous medium, successively, disposed in the first branch of the flow manifold, measuring a second flow rate of the second portion of the fluid using a second flowmeter disposed on a cross flow line fluidly connecting the first coil and the second coil, adjusting, using a flow control device disposed immediately downstream of the control coil, the first flow rate of the fluid in the first inlet line until the second flow rate is equal to zero. The method further includes calculating a transmissibility of the first coil, the second coil, and the control coil and calculating a permeability of the porous medium.

Other aspects and advantages of the claimed subject matter will be apparent from the following description and the appended claims.

DETAILED DESCRIPTION

Figure 1:
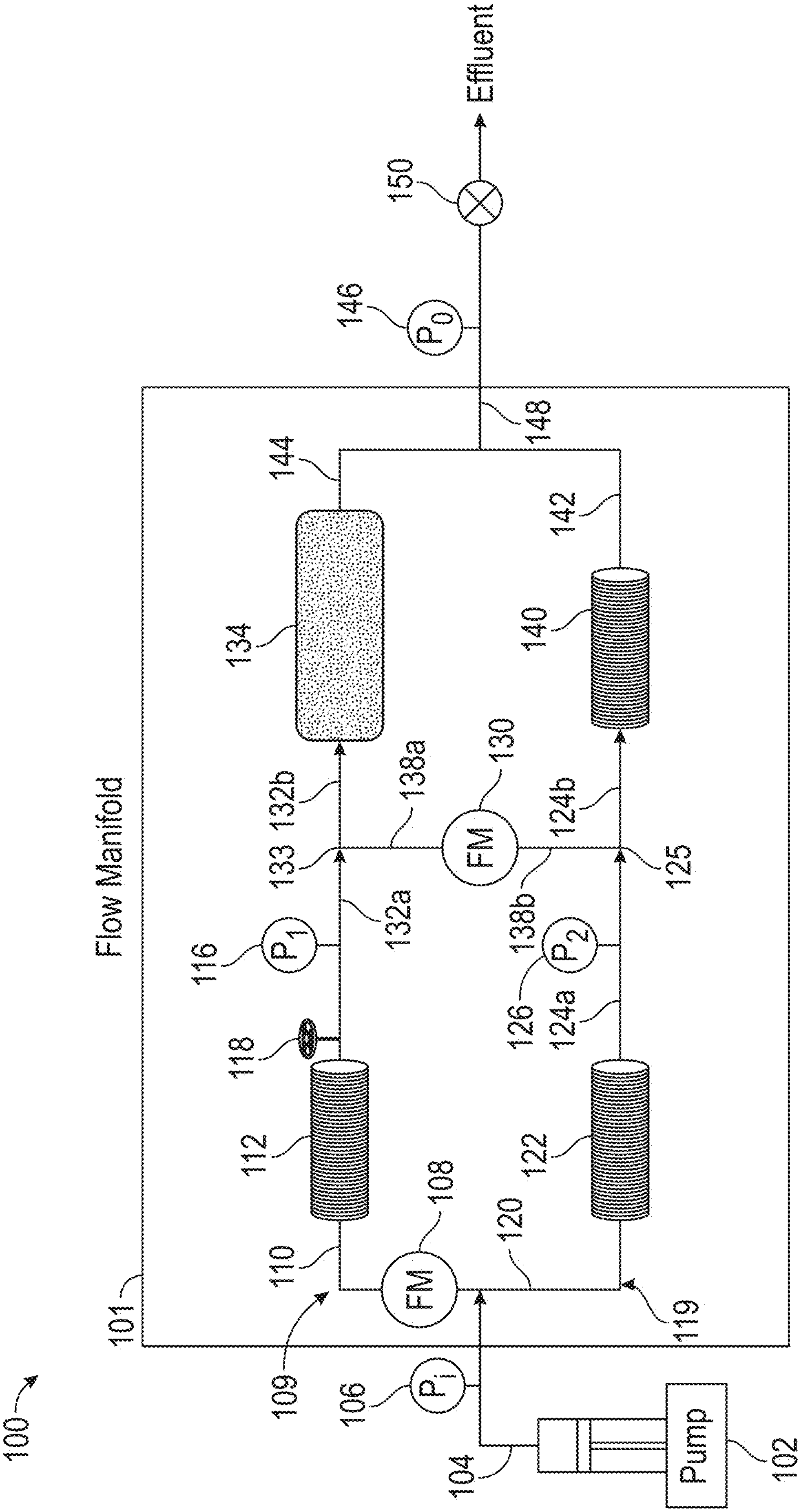
FIG. 1 is a system according to one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (for example, first, second, third) may be used as an adjective for an element (that is, any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "a fluid sample" includes reference to one or more of such samples.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowcharts may be omitted, repeated, and/or performed in a different order than the order shown. Accordingly, the scope of the invention should not be considered limited to the specific arrangement of steps shown in the flowcharts.

Although multiply dependent claims are not introduced, it would be apparent to one of ordinary skill that the subject matter of the dependent claims of one or more embodiments may be combined with other dependent claims.

Measuring pressure drop when a fluid flows through a porous medium is usually accomplished by using pressure gauges at an upstream and a downstream position of the porous medium. Pressure drop through a porous medium may also be measured using a differential pressure transducer with two legs spanning across the porous medium. When the pressure drop is low, for example when a fluid flows through a high permeability rock, highly accurate and sensitive pressure transducers may be required in order to detect the small pressure difference. Such transducers are costly and frequently need re-calibration. Embodiments described herein generally relate to systems and methods for measuring low differential pressure across a porous medium without using high resolution, high accuracy pressure transducers.

"Porosity" is defined herein as a percent of open space within a volume of solid material.

"Transmissibility" is defined herein as a property of a porous medium, which measures the capacity of the porous medium to transmit a specific fluid. The transmissibility of the porous medium depends on characteristics of the porous medium and the specific fluid.

"Permeability" is defined herein as a physical property of a porous medium, which describes the rate of water movement through interconnected pores within the porous medium.

Embodiments disclosed herein relate to a system for measuring low differential pressure of a flowing fluid. The system according to one or more embodiments includes an inlet line, a flow manifold, and an effluent line.

FIG. 1 illustrates the system 100 for measuring low differential pressure of a flowing fluid of one or more embodiments. The system 100 includes an inlet line 104 which includes an inlet pressure gauge 106 configured to measure an inlet pressure of fluid in the inlet line 104.

The system 100 also includes a flow manifold 101 which may be used according to one or more embodiments to measure low differential pressure across a porous medium. The inlet line 104 is fluidly connected to the flow manifold 101. The flow manifold 101 includes a first branch 109 and a second branch 119. Upon entering the flow manifold 101, the inlet line 104 is split into a first inlet line 110 in the first branch 109 and a second inlet line 120 in the second branch 119. In one or more embodiments, a pump 102 is fluidly connected upstream of the inlet line 104. The pump 102 is configured to pump a fluid through the inlet line 104 and subsequently into the flow manifold 101. The pump 102 may be configured to provide fixed pressure within the flow manifold 101 or a fixed flow rate of the fluid. The pump may be any suitable pump known in the art capable of pressurizing a fluid and providing it to the flow manifold. For example, the pump may be a positive-displacement pump, a centrifugal pump, an axial-flow pump, or the like. In general, the pump size and design may be selected based on the specific fluid to be pumped.

The first branch 109 of the flow manifold 101 includes a first flow meter 108 configured to measure a first flow rate of fluid in the first inlet line 110. The first branch also includes a pressure control system 112 located downstream of the first flow meter 108. The pressure control system 112 may include a control coil 114 and a flow control device 118, located immediately downstream of the control coil 114. A first flow line **132*a* exits the pressure control system 112. A flow rate of fluid in the first flow line 132*a* may be controlled by opening or closing the flow control device 118 to adjust the amount of fluid flowing through the first inlet line 110, through the control coil 114, and into the first flow line 132*a*. The first flow line 132*a* includes a first pressure gauge 116 configured to measure a pressure of fluid in the first flow line 132**.

At a point downstream of the first pressure gauge 116, the first flow line **132*a* is fluidly connected, at approximately a 90° angle, to a cross flow line 138. A first junction point 133 exists where fluid may flow from the first flow line 132*a* to either a first portion of the first cross flow line 138*a* or the fluid may continue to flow straight to a second portion of the first flow line 132*b*, located downstream of the first junction point 133**.

The first branch 109 also includes a porous medium 134 of unknown permeability located immediately downstream from the first junction point 133. The second portion of the first flow line **132*b* enters the porous medium 134, where fluid in the first flow line undergoes a pressure drop across the porous medium 134. A first outlet line 144 exits the porous medium 134**.

The second branch 119 includes a first coil 122 and a second coil 140 having a known hydraulic conductivity (permeability equivalence). The second inlet line 120 enters the first coil 122, where a fluid in the second inlet line 120 experiences a pressure drop as it flows through the first coil 122. Because the permeability, length, inner diameter, and other parameters associated with the first coil 122 are known, the change in pressure in the fluid as it flows through the first coil 122 may be calculated. Details of the calculation will be provided in the "Methods" section, below.

A second flow line **124*a* exits the first coil 122. The second flow line 124*a* includes a second pressure gauge 126 configured to measure a pressure of fluid in the second flow line 124*a*. At a point downstream of the second pressure gauge 126, the second flow line 124*a* is fluidly connected, at approximately a 90° angle, to a cross flow line 138. A second junction point 125 exists where fluid may flow from the second flow line 124*a* to either a second portion of the second cross flow line 138*b* or the fluid may continue to flow straight to a second portion of the second flow line 124*b*, located downstream of the second junction point 125**.

The cross flow line 138 also includes a second flow meter 130, located between the first cross flow line **138*a* and the second cross flow line 138*b*. The second flow meter 130 is configured to measure a flow rate of fluid in the cross flow line 138**.

The second branch 119 also includes a second coil 140 located downstream of the second junction point 125. The second portion the second flow line **124*b* enters the second coil 140, where a fluid in the second portion of the second flow line 124*b* experiences a pressure drop as it flows through the second coil 140. Because the permeability, length, inner diameter, and other parameters associated with the second coil 140 are known, the change in pressure in the fluid as it flows through the second coil 140 may be calculated. A second outlet line 142 exits the second coil 140**.

The pressure control system 112, and the flow control device 118, in the first branch 109 may be used to control a flow rate of fluid in the first flow line 132*a* such that the differential flow rate as measured by the second flow meter 130 (and therefore the differential pressure) between the fluid in the first flow line 132*a* and the second portion of the first flow line 132*b* and in the second flow line 124*a* and the second portion of the second flow line 124*b* is zero. Accordingly, when the pressure differential between the first flow line 132*b* and the second flow line 124*a* is zero, the pressure difference between the first branch 109 and the second branch 119 is also zero such that no fluid flows across the first cross flow line 138*a* and the second cross flow line 138*b* and the second flow meter 130 will read a value of zero.

The first outlet line 144 and the second outlet line 142 combine to produce an effluent line 148. The effluent line 148 exits the flow manifold 101. An outlet pressure gauge 146 is disposed on the effluent line 148 and is configured to measure a pressure of fluid in the effluent line 148. A back pressure regulator 150 is also disposed on the effluent line 148. The back pressure regulator 150 is configured to maintain a desired pressure in the effluent line 148 and flow manifold 101.

The term "flow manifold" is used herein to refer to a fluid distribution system or device that brings valves or tubing into one place or a single channel into an area where many points meet. Flow manifold systems can range from simple supply chambers with several outlets, to multi-chambered flow control units. The overall flow manifold according to one or more embodiments resembles a Wheatstone Bridge electric circuit.

The fluid of one or more embodiments is any Newtonian fluid having known properties, such as a known dynamic viscosity. For example, the fluid may be water, honey, glycol, alcohol, mineral oil, kerosene, diesel, combinations thereof, and the like.

The inlet pressure gauge, the first pressure gauge, the second pressure gauge, and the outlet pressure gauge may be any pressure gauge known in the art capable of measuring a fluid pressure. For example, the pressure gauge of one or more embodiments may be a bourdon tube pressure gauge, a diaphragm pressure gauge, a capsule pressure gauge, an absolute pressure gauge, a bellows pressure gauge, or the like.

The first flow meter and the second flow meter may be any flow meter known in the art capable of measuring a fluid flow rate. The first flow meter and the second flow meter of one or more embodiments may be an ultrasonic flow meter, a vortex flow meter, a magnetic flow meter, a turbine flow meter, a paddle wheel flow meter, and the like.

The first coil and the second coil according to one or more embodiments may be any tubing known in the art, such as a coiled tubing. In the art, tubing may refer to different types of pipes, such as tubing, drill pipe, casing, coiled tubing, etc., used as conduits for fluids in an oil or gas well. The first coil and the second coil may be two known hydraulic conductivity (permeability equivalence) coils with a known length.

The pressure control system may include a number of components, including but not limited to, a control coil, and a flow control device. The control coil may be any tubing known in the art, such as coiled tubing, having a known hydraulic conductivity. The flow control device may be a choke valve, orifice, needle valve, or the like. A flow meter is connected to the flow control mechanism to measure the flow rate through the first branch. The location of the first flow meter may be as shown by the first flow meter 108 in FIG. 1, or the first flow meter may be located downstream of the pressure control system 112 in-line with the first pressure gauge 116 on the first branch 109. The flow control device may be configured to reduce or increase a flow rate of fluid in the first flow line. The pressure control system of one or more embodiments is an adjustable pressure drop control segment.

The porous medium may be any porous medium of interest. For example, the porous medium may be a sand pack, sand, rock, gravel, sandstone, limestone, dolomite, or the like. The porous medium may also be a filtration material such as a polymer, a cloth, a ceramic, or the like.

Systems and methods of one or more embodiments may be advantageously used to measure any porous medium having a permeability in a range of from about 100 milli Darcy to about 1 million milli darcy. For example, the porous medium may have a permeability having a lower limit selected from 100 milli Darcy, 500 milli Darcy, 1,000 milli Darcy, and 10,000 milli Darcy to an upper limit selected from 50,000 milli Darcy, 100,000 milli Darcy, 500,000 milli Darcy, and 1,000,000 milli Darcy, where any lower limit may be paired with any upper limit. In particular, systems and methods according to one or more embodiments may be advantageously used to measure a permeability of a porous medium having a relatively high permeability accurately, and cost effectively, without the use of a transducer or other costly equipment.

The back pressure regulator 150 of one or more embodiments may be any type of back pressure regulator known in the art capable of regulating an upstream pressure. For example, the back pressure regulator may be self-operated, high flow, differential, vacuum, air loaded, pilot operated, or the like.

A differential pressure across the porous medium according to one or more embodiments is relatively low. For example, the differential pressure across the porous medium may be in a range of from about 0.1 psi to about 1 psi. For example, the pressure differential may be in a range having a lower limit selected from about 0.1, 0.2, and 0.5 psi to an upper limit selected from about 0.7, 0.9, and 1.0 psi, where any lower limit may be paired with any upper limit.

Method for Measuring Permeability of a Porous Medium

When a fluid flows through a porous medium, the fluid pressure typically decreases (known as pressure drop). Due to the simple geometry of the tubing, the relationship between the pressure drop and flow rate through these coiled tubing is known. Therefore, the equivalent permeability can be determined for these coils. The function of the adjustable pressure control valve and coil is to ensure flow rate (or pressure differential) to be zero between the first branch and the second branch. In one or more embodiments, when fluid is injected through the flow manifold, the differential pressure of the target medium can be accurately calculated by the differential pressures of the known pressure drop segments and adjustable pressure drop control segment.

Figure 2:
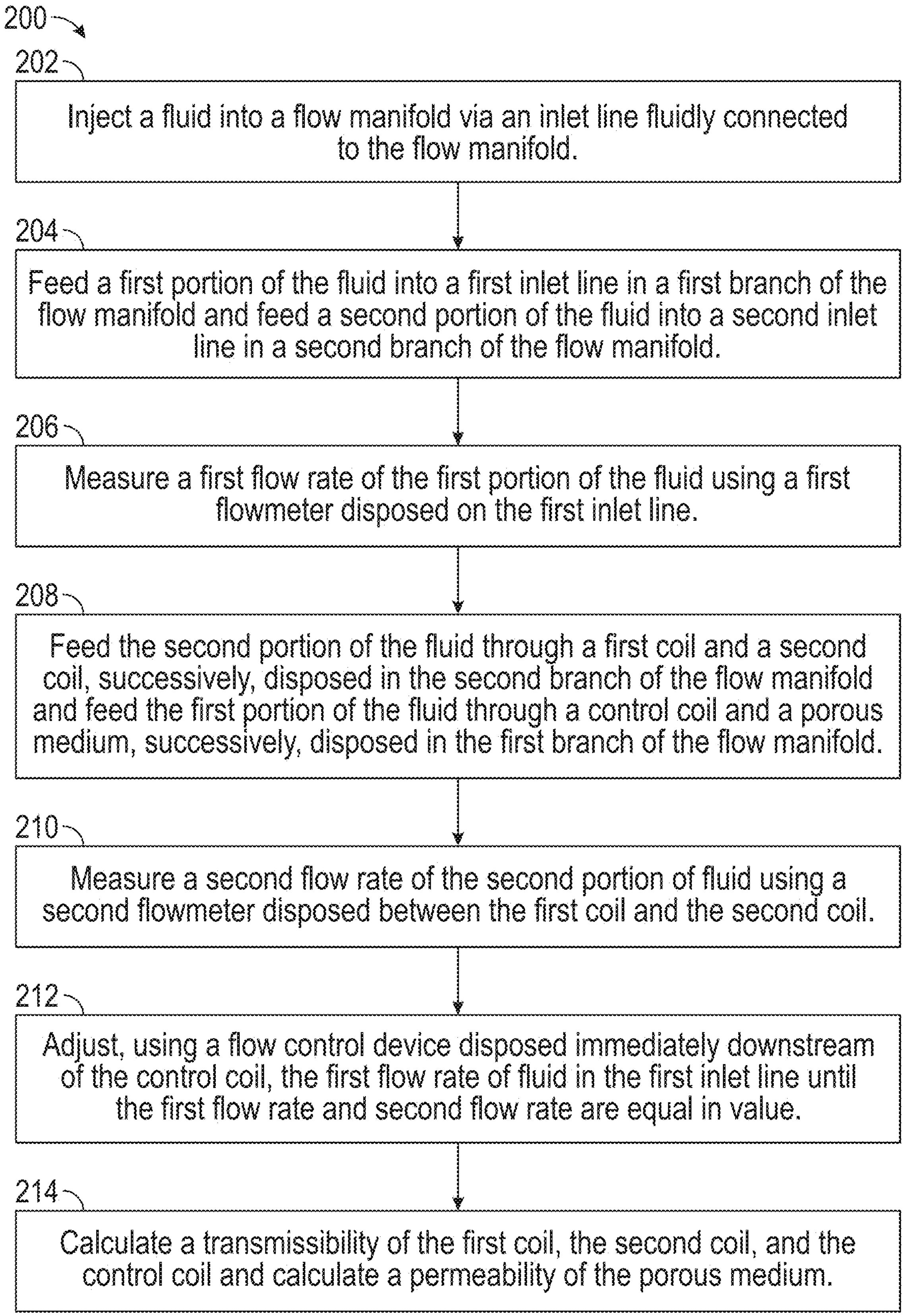
FIG. 2 is a flowchart of a method according to one or more embodiments.

The method for measuring permeability of a porous medium according to one or more embodiments is summarized in the flowchart of FIG. 2. The method 200 includes, in step 202, injecting a fluid into a flow manifold via an inlet line fluidly connected to the flow manifold. In some embodiments, the fluid is water.

The method 200 also includes, in step 204, feeding a first portion of the fluid into a first inlet line in a first branch of the flow manifold and feeding a second portion of the fluid into a second inlet line in a second branch of the flow manifold.

The method 200 further includes measuring, in step 206, a first flow rate of the first portion of the fluid using a first flowmeter disposed on the first inlet line.

The method 200 further includes, in step 208, feeding the second portion of the fluid through a first coil and a second coil, successively, disposed in the second branch of the flow manifold and feeding the first portion of the fluid through a control coil and a porous medium, successively, disposed in the first branch of the flow manifold.

The method 200 also includes, in step 210, measuring a second flow rate of the second portion of fluid using a second flowmeter disposed between the first coil and the second coil.

The method 200 also includes, in step 212, adjusting, using a flow control device disposed immediately downstream of the control coil, the first flow rate of fluid in the first inlet line until the first flow rate and second flow rate are equal in value. In some embodiments, the flow control device is a needle valve and the adjusting further includes opening the needle valve to allow the fluid to flow through the first inlet line and through the control coil, measuring a first adjusted flow rate using the first flowmeter and a second adjusted flow using the second flowmeter, and repeating the above steps until the first flow rate and the second flow rate are equal in value.

Further, the method 200 includes, in step 214, calculating a transmissibility of the first coil, the second coil, and the control coil and calculating a permeability of the porous medium. In some embodiments, calculating the transmissibility of the control coil, the first coil, and the second coil further includes using Equations 1, 2, and 3:

$$T_1 = \frac{\pi D_1^4}{128\mu} \quad \text{(Equation 1)}$$

$$T_2 = \frac{\pi D_2^4}{128\mu} \quad \text{(Equation 2)}$$

$$T_a = \frac{\pi D_a^4}{128\mu} \quad \text{(Equation 3)}$$

where, $T_1$ is the transmissibility of the first coil, $T_2$ is the transmissibility of the second coil, $T_a$ is the transmissibility of the control coil, $D_1$ is a diameter of the first coil, $D_2$ is a diameter of the second coil, $D_a$ is a diameter of the control coil, and μ is a dynamic viscosity of the fluid flowing through the flow manifold.

Finally, the method 200 includes, in step 212, calculating a permeability of a porous medium, where the porous medium is located in the first branch of the flow manifold, downstream of the flow control device, and wherein the first flow line enters the porous medium. In some embodiments, the porous medium has a permeability in a range of from about 100 milli Darcy to about 1,000,000 milli Darcy. In some embodiments, calculating the permeability of the porous medium includes using Equation 4:

$$K = \frac{T_a T_2 \mu L}{T_1 A} \quad \text{(Equation 4)}$$

where, $T_1$ is the transmissibility of the first coil, $T_2$ is the transmissibility of the second coil, $T_a$ is the transmissibility of the control coil, μ is a dynamic viscosity of the fluid flowing through the flow manifold, L is a length of the porous medium, and A is a cross-sectional area of the porous medium.

Examples

Example 1 is a description of how Equations 1, 2, 3, and 4 from the "Method," above are derived. In the flow manifold represented by the system of FIG. 1, a flow rate of fluid traveling through the first coil and the second coil is represented by Equations 4 and 5, below.

$$Q_1 = T_1(P_i - P_2) \quad \text{(Equation 4)}$$

$$Q_2 = T_2(P_2 - P_o) \quad \text{(Equation 5)}$$

Where $Q_1$ and $Q_2$ are the flow rates flowing through the first coil and the second coil, respectively, $T_1$ and $T_2$ are the transmissibility of the first coil and the second coil, respectively, $P_i$ is a fluid pressure measured from the inlet pressure gauge, $P_2$ is a fluid pressure measured from the second pressure gauge, and $P_o$ is a fluid pressure measured from the outlet pressure gauge.

Similarly, a flow rate of fluid flowing through the control coil and the porous medium are represented by Equations 6 and 7, respectively, below.

$$Q_a = T_a(P_i - P_1) \quad \text{(Equation 6)}$$

$$Q_x = T_x(P_1 - P_o) \quad \text{(Equation 7)}$$

Where $Q_a$ is a flow rate of fluid flowing through the control coil measured by the first flow meter, $P_1$ is a pressure measured by the first pressure gauge, $P_i$ is a fluid pressure measured from the inlet pressure gauge, and $T_a$ is the transmissibility of the control coil. $Q_x$ is a flow rate of fluid flowing through the porous medium, $P_1$ is a pressure measured by the first pressure gauge, $P_o$ is a fluid pressure measured from the outlet pressure gauge, and $T_x$ is the transmissibility of the porous medium.

The transmissibility of known coils is calculated as follows. Pressure drop as a function of fluid flow rate through a coil of known inner diameter and length can be described by the Darcy-Weisbach equation, shown in Equation 8, below:

$$\frac{\Delta P}{L} = \frac{128\,\mu}{\pi} \frac{Q}{D_H^4} \quad \text{(Equation 8)}$$

Where ΔP is a pressure differential, defined as an outlet pressure of fluid exiting a coil subtracted from an inlet pressure of fluid entering the coil, L is a length of the coil, μ is a dynamic viscosity of the fluid, Q is a flow rate of fluid traveling through the oil, and $D_H$ is a hydrodynamic diameter of the coil.

Applying the Darcy-Weisbach equation (Equation 8) to Equations 4, 5, and 6, the transmissibility of the first coil, the second coil, and the control coil may be determined using Equations 1, 2 and 3, respectively, shown below.

$$T_1 = \frac{\pi D_1^4}{128\ \mu} \quad \text{(Equation 1)}$$

$$T_2 = \frac{\pi D_2^4}{128\ \mu} \quad \text{(Equation 2)}$$

$$T_a = \frac{\pi D_a^4}{128\ \mu} \quad \text{(Equation 3)}$$

In the method of one or more embodiments, the flow control device is adjusted to ensure that there is no flow difference between the first branch of the flow manifold and the second branch of the flow manifold, therefore:

$$Q_1 = Q_2 \quad \text{(Equation 9)}$$

$$Q_a = Q_x \quad \text{(Equation 10)}$$

$$P_1 = P_2 \quad \text{(Equation 11)}$$

Applying Equations 9, 10, and 11 to Equations 4 and 5 yields:

$$T_1(P_i - P_2) = T_2(P_2 - P_o) \quad \text{(Equation 12)}$$

Rearranging Equation 12, $$\frac{T_1}{T_2} = \frac{P_2 - P_o}{P_i - P_2} \quad \text{(Equation 13)}$$

And, $$T_a(P_i - P_1) = T_x(P_1 - P_o) \quad \text{(Equation 14)}$$

Rearranging Equation 14, $$\frac{T_a}{T_x} = \frac{P_1 - P_o}{P_i - P_1} \quad \text{(Equation 15)}$$

Applying Equation 11 to Equations 13 and 15, $$\frac{T_1}{T_2} = \frac{T_a}{T_x} \quad \text{(Equation 16)}$$

Therefore, the transmissibility of the porous medium may be determined by Equation 17, below.

$$T_x = \frac{T_a T_2}{T_1} \quad \text{(Equation 17)}$$

Based on the definition of the transmissibility of a porous medium, $$T_x = \frac{KA}{\mu L} \quad \text{(Equation 18)}$$

Therefore, $$K = \frac{T_x \mu L}{A} \quad \text{(Equation 19)}$$

And, combining Equation 17 with Equation 19, permeability of the porous medium is determined by Equation 4, below.

$$K = \frac{T_a T_2 \mu L}{T_1 A} \quad \text{(Equation 4)}$$

Where $T_x$ is transmissibility of the porous medium, K is permeability of the porous medium A is a cross-sectional area of the porous medium, μ is dynamic viscosity of fluid flowing through the porous medium, and L is a length of the porous medium.

Example 2 is a demonstration of how permeability of a porous medium may be calculated using the systems and methods of one or more embodiments. A high permeability sand pack, of which the permeability needs to be measured experimentally, is connected as illustrated in the system 100 of FIG. 1. The sand pack has a diameter of 1 inch and a length of 6 inches. The first coil consists of stainless steel coiled tubing having a length of 30 ft and 1/16" inner diameter. The second coil consists of stainless steel coiled tubing having a length of 50 ft and 1/8" inner diameter. The pressure control system consists of stainless steel coiled tubing having a length of 20 ft and 1/8" inner diameter, and a 1/16" needle valve.

The transmissibility of the first coil ($T_1$) is calculated to be 103 cc/min/atm using Equation 1, the transmissibility of the second coil ($T_2$) is calculated to be 995 cc/min/atm using Equation 2. Water is injected through the flow manifold, and the flow control device (in this case, a needle valve) is adjusted so that there is no flow between the first and second branches as measured by the flow meter on the cross flow line. Upon doing so, the first flow meter and the first pressure gauge read 1 cc/min and 8.5 psi, respectively. The transmissibility of the control coil ($T_a$) is calculated to be 1.7 cc/min/atm using Equation 6. The sand pack has a cross sectional area of 5.06 $cm^2$, a length of 156.24 cm, and the dynamic viscosity of water at ambient temperature (μ) is 1 cP. Applying Equation 18, a transmissibility of the targeted porous media (i.e., the sand pack) is calculated to be 16.4 cc/min/atm. And applying Equation 19, the permeability of the sand pack is calculated to be 2964 Darcy.

In the known art, an injection pump pumping fluid at about 100 cc/min and a differential pressure transducer accurate at about 0.025 psi will be needed to measure such a high permeability porous medium as described in Example 2. In typical laboratory equipment according to a method of prior art, pump rates may be in a range from about 0.5 to 60 cc/min and differential pressure transducers may measure a pressure in a range of from about 0.5 to 500 psi. Accordingly, the pressure drop across a porous medium that is 2964 Darcy in permeability will be 0.025 psi with a pump injection rate of 100 cc/min. It is unlikely that a common pressure transducer can accurately measure such low pressure differential. Hence, the systems and methods according to one or more embodiments may be advantageously employed to determine permeability of a high permeability porous medium in a cost effective and accurate manner.

What is claimed:

1. A system for measuring permeability of a porous medium, comprising:

an inlet line comprising an inlet pressure gauge, wherein a fluid is injected into the inlet line;

a flow manifold, comprising, a first branch, comprising:

a first inlet line comprising a first flow meter;

a pressure control system, located downstream of the first flow meter, comprising a control coil and a flow control device located immediately downstream of the control coil;

a first flow line, exiting the pressure control system, a first junction point, fluidly connected to the first flow line and a cross flow line, wherein the cross flow line comprises a second flow meter;

a porous medium, located downstream of the first junction point; and a first outlet line, wherein the first flow line enters the porous medium and the first outlet line exits the porous medium, and a second branch, comprising:

a second inlet line;

a first coil, wherein the second inlet line is fluidly connected to an upstream side of the first coil;

a second flow line, exiting the first coil;

a second junction point, fluidly connected to the first flow line through the cross flow line;

a second coil, wherein the second flow line enters the second coil; and a second outlet line exiting the second coil;

wherein the cross flow line connects the first branch to the second branch; and an effluent line, wherein the first outlet line and the second outlet line combine to produce the effluent line.

2. The system of claim 1, further comprising:

a first pressure gauge disposed on the first flow line;

a second pressure gauge disposed on the second flow line; and an outlet pressure gauge disposed on the effluent line.

3. The system of claim 1, further comprising:

a pump, fluidly connected upstream of the inlet line, configured to pump the fluid through the inlet line and into the flow manifold.

4. The system of claim 1, further comprising:

a back pressure regulator located on the effluent line.

5. The system of claim 1, wherein the fluid is water.

6. The system of claim 1, wherein the first coil, the second coil, and the control coil are a coiled tubing.

7. The system of claim 1, wherein the flow control device is a needle valve.

8. The system of claim 1, wherein the porous medium has a permeability in a range of from about 100 milli Darcy to about 1,000,000 milli Darcy.

9. A method for measuring permeability of a porous medium, comprising:

injecting a fluid into a flow manifold via an inlet line fluidly connected to the flow manifold, feeding a first portion of the fluid into a first inlet line in a first branch of the flow manifold;

feeding a second portion of the fluid into a second inlet line in a second branch of the flow manifold;

measuring a first flow rate of the first portion of the fluid using a first flowmeter disposed on the first inlet line;

feeding the second portion of the fluid through a first coil and a second coil, successively, disposed in the second branch of the flow manifold;

feeding the first portion of the fluid through a control coil and a porous medium, successively, disposed in the first branch of the flow manifold;

measuring a second flow rate of the second portion of the fluid using a second flowmeter disposed on a cross flow line fluidly connecting the first coil and the second coil;

adjusting, using a flow control device disposed immediately downstream of the control coil, the first flow rate of the fluid in the first inlet line until the second flow rate is equal to zero, calculating a transmissibility of the first coil, the second coil, and the control coil; and calculating a permeability of the porous medium.

10. The method of claim 9, wherein calculating the transmissibility of the first coil, the second coil, and the control coil further comprises using Equation 1, Equation 2, and Equation 3:

$$T_1 = \frac{\pi D_1^4}{128\,\mu} \quad \text{(Equation 1)}$$

$$T_2 = \frac{\pi D_2^4}{128\,\mu} \quad \text{(Equation 2)}$$

$$T_a = \frac{\pi D_a^4}{128\,\mu} \quad \text{(Equation 3)}$$

wherein, $T_1$ is the transmissibility of the first coil, $T_2$ is the transmissibility of the second coil, $T_a$ is the transmissibility of the control coil, $D_1$ is a diameter of the first coil, $D_2$ is a diameter of the second coil, $D_a$ is a diameter of the control coil, and u is a dynamic viscosity of the fluid flowing through the flow manifold.

11. The method of claim 9, wherein calculating the permeability of the porous medium further comprises using Equation 4:

$$K = \frac{T_a T_2 \mu L}{T_1 A} \quad \text{(Equation 4)}$$

wherein, $T_1$ is the transmissibility of the first coil, $T_2$ is the transmissibility of the second coil, $T_a$ is the transmissibility of the control coil, μ is a dynamic viscosity of the fluid flowing through the flow manifold, L is a length of the porous medium, and A is a cross-sectional area of the porous medium.

12. The method of claim 9, wherein the fluid is water.

13. The method of claim 9, wherein the first coil, the second coil, and the control coil are a coiled tubing.

14. The method of claim 9, wherein the flow control device is a needle valve and the adjusting further comprises:

opening the needle valve to allow the fluid to flow through the first inlet line and through the control coil;

measuring a first adjusted flow rate using the first flowmeter and a second adjusted flow using the second flowmeter; and repeating the above steps until the second flow rate is equal to zero.

15. The method of claim 9, wherein the porous medium has a permeability of greater in a range of from about 100 milli Darcy to about 1,000,000 milli Darcy.

* * * * *